United States Patent
Abels et al.

(10) Patent No.: US 7,293,987 B2
(45) Date of Patent: *Nov. 13, 2007

(54) ADJUSTABLE BITE RAMPS FOR DEEP BITE CORRECTION AND KITS INCORPORATING BITE RAMPS

(76) Inventors: Norbert Abels, Alleestrasse 30a, 66424 Homburg (DE); Claus-H. Backes, St. Wendeler Strasse 45, 66113 Saarbrücken (DE)

( * ) Notice: Subject to any disclaimer, the term of this patent is extended or adjusted under 35 U.S.C. 154(b) by 99 days.

This patent is subject to a terminal disclaimer.

(21) Appl. No.: 10/835,963

(22) Filed: Apr. 30, 2004

(65) Prior Publication Data

US 2005/0244778 A1     Nov. 3, 2005

(51) Int. Cl.
  *A61C 3/00* (2006.01)
(52) U.S. Cl. ...................................................... 433/18
(58) Field of Classification Search ................ 433/180, 433/7, 18, 19, 6, 8, 2, 22, 24, 39
  See application file for complete search history.

(56) References Cited

U.S. PATENT DOCUMENTS

| 1,133,379 | A | * | 3/1915 | Hollingsworth | 433/39 |
| 2,645,014 | A | * | 7/1953 | Mathison | 433/39 |
| 3,798,773 | A | | 3/1974 | Northcutt | 32/14 |
| 4,480,994 | A | | 11/1984 | Hoffman | 433/6 |
| 4,525,143 | A | | 6/1985 | Adams | 433/5 |
| 4,773,853 | A | * | 9/1988 | Kussick | 433/6 |
| 4,773,857 | A | * | 9/1988 | Herrin | 433/138 |
| 4,915,630 | A | | 4/1990 | Honig | 433/215 |
| 5,067,896 | A | | 11/1991 | Korn | 433/6 |
| 5,160,260 | A | * | 11/1992 | Chang | 433/8 |
| 5,505,618 | A | * | 4/1996 | Summer | 433/148 |
| 5,564,927 | A | * | 10/1996 | Barnes et al. | 433/179 |
| 5,683,244 | A | | 11/1997 | Truax | 433/6 |
| 5,718,575 | A | * | 2/1998 | Cross, III | 433/6 |
| 5,769,103 | A | * | 6/1998 | Turjak | 132/329 |
| 5,799,797 | A | * | 9/1998 | Braun | 206/586 |
| 5,848,891 | A | * | 12/1998 | Eckhart et al. | 433/19 |
| 5,885,073 | A | * | 3/1999 | Kussick | 433/6 |
| 5,957,686 | A | * | 9/1999 | Anthony | 433/19 |
| 6,309,215 | B1 | * | 10/2001 | Phan et al. | 433/24 |
| 6,364,659 | B1 | | 4/2002 | Lotte | 433/8 |
| 6,368,106 | B1 | | 4/2002 | Clark | 433/19 |
| 6,413,082 | B2 | | 7/2002 | Binder | 433/19 |
| 6,464,494 | B1 | * | 10/2002 | Young | 433/18 |
| 6,464,495 | B1 | | 10/2002 | Voudouris | 433/18 |

(Continued)

OTHER PUBLICATIONS

Ormco Products Guide, "Bite Turbos", Section 9, p. 3, vol. 6, No. 1, 1997.

(Continued)

*Primary Examiner*—Cary E. O'Connor
(74) *Attorney, Agent, or Firm*—Workman Nydegger (57) ABSTRACT

An adjustable bite ramp includes a tooth-attachment element and ramp element. The tooth-attachment element is sized and configured for bonding to the lingual surface of a person's tooth, while the ramp element is hingedly or bendably adjustable relative to the tooth-attachment element. The ramp element provides a ramp at a desired angle for engaging a corresponding tooth of the opposite dental arch when the person's mouth is closed. The engagement between the ramp element and the corresponding tooth of the opposite dental arch causes the lower jaw to move forward relative to the upper jaw, thereby incrementally correcting the deep bite condition.

23 Claims, 6 Drawing Sheets

U.S. PATENT DOCUMENTS

| | | |
|---|---|---|
| 6,592,366 B2 | 7/2003 | Triaca et al. .................... 433/7 |
| 6,613,001 B1 | 9/2003 | Dworkin ..................... 600/590 |
| 6,626,665 B1 | 9/2003 | Keles ......................... 433/18 |
| 6,726,473 B1* | 4/2004 | Guray ........................... 433/6 |
| 2003/0198911 A1* | 10/2003 | Knopp et al. ................. 433/6 |
| 2004/0009450 A1 | 1/2004 | Clark .......................... 433/18 |
| 2004/0115592 A1* | 6/2004 | Zilberman ................. 433/218 |
| 2004/0224277 A1* | 11/2004 | Kussick ........................ 433/6 |

OTHER PUBLICATIONS

Ultradent Product Packaging Instructions, "Opal Adjustable Bite Ramp" May 26, 2004.

* cited by examiner

ADJUSTABLE BITE RAMPS FOR DEEP BITE CORRECTION AND KITS INCORPORATING BITE RAMPS

BACKGROUND OF THE INVENTION

1. The Field of the Invention

The present invention is in the field of orthodontics, more particularly to apparatus and methods for the correction of class II malocclusions and/or "deep bite," also known as "overbite".

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth or the jaw to correct underbites or overbites. For example, orthodontic treatment can improve the patient's occlusion, or enhanced spatial matching of corresponding teeth.

Overbite, also known as "deep bite," occurs when there is excessive vertical overlap of the incisors. Deep bite can result in increased wear of the incisors, periodontal problems, increasingly visible gum tissue, and increased instances of the patient biting the roof of their mouth. In addition, correction of a deep bite condition often results in a more aesthetically appealing smile for the patient.

Depending on the severity of the deep bite condition, correction can sometimes be achieved with installation and use of dental braces, although orthognathic surgery is sometimes required. Installation of dental braces can be ineffective in effecting sufficient movement of the jaw, while orthognathic surgery is expensive, invasive, and uncomfortable, especially from a patient's perspective.

Therefore, there exists a need for devices and kits that can be used to provide less expensive, simpler, less invasive deep bite correction.

BRIEF SUMMARY OF THE PREFFERED EMBODIMENTS

The adjustable bite ramps of the present invention include a tooth-attachment element and a ramp element. The tooth-attachment element is sized and configured for bonding to the lingual surface of a person's front tooth (e.g., an upper or lower incisor and/or canine), while the ramp element is hingedly or bendably adjustable relative to the tooth-attachment element. The ramp element provides a ramp structure at a desired angle for engaging the corresponding teeth of the opposite dental arch (e.g., the upper or lower incisors and/or canines) when the person's mouth is closed. The engagement between the ramp structure and the corresponding teeth of the opposite dental arch causes the lower jaw to move forward relative to the upper jaw, while also disoccluding the lateral teeth and allowing a new neutral occlusion. The bite ramps may also be used in combination with class II elastics to move the lower jaw forward.

The adjustable bite ramps may be made from metal, plastic, or another somewhat flexible material so as to allow adjustment of the ramp element. Suitable metals include stainless steel, titanium, and titanium alloys. Preferably, any metals used are nickel free or have a low nickel content so as to avoid patient sensitivity which can sometimes be caused by nickel. According to one embodiment, the adjustable ramps may be injection molded from a plastic.

The adjustable bite ramps may further comprise means for locking the ramp element in a desired adjustment angle relative to the tooth-attachment element. An example of such a means for locking is a curable resin that is applied to and cured between the tooth-attachment and ramp elements. The cured resin locks the ramp element in a desired adjustment angle, and provides a more comfortable surface for the patient's tongue and soft tissues.

According to one embodiment, an optional shoe may be placed over the adjustable bite ramp. The shoe may be bonded to the adjustable bite ramp with an adhesive. In use, the lower surface of the shoe provides the ramp for engaging the corresponding tooth of the opposite dental arch. The upper surface provides a smoother surface within the patient's mouth (e.g., to provide enhanced comfort and/or to help prevent buildup of plaque or other foreign matter).

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The adjustable bite ramps of the present invention include a tooth-attachment element and a ramp element. The tooth-attachment element is sized and configured for bonding to the lingual surface of a person's tooth (e.g., an upper incisor), while the ramp element is hingedly or bendably adjustable relative to the tooth-attachment element. The ramp element provides a ramp structure at a desired angle for engaging the corresponding tooth of the opposite dental arch (e.g., the lower incisor) when the person's mouth is closed. The engagement between the ramp and the corresponding teeth of the opposite dental arch causes the lower jaw to move forward relative to the upper jaw. In some cases, forward movement of the lower jaw may be assisted by the use of class II elastics attached to, e.g., the lower end molars and the upper canines.

II. Exemplary Adjustable Bite Ramp

Figure 1A:
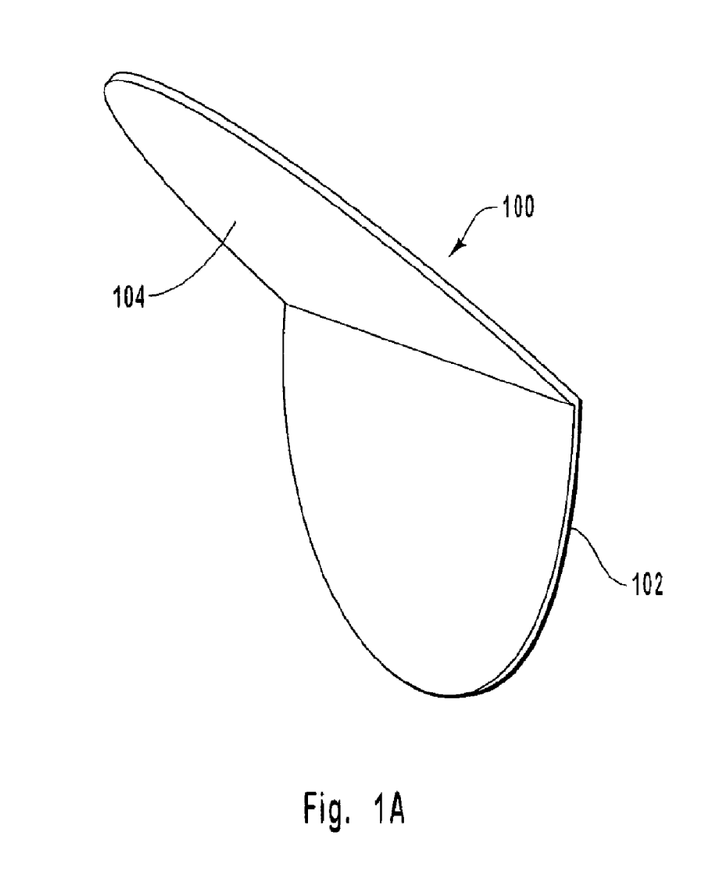
FIG. 1A is a perspective view of an exemplary adjustable bite ramp according to the invention.

FIG. 1A illustrates an exemplary adjustable bite ramp 100. The adjustable bite ramp 100 includes a tooth-attachment element 102 and a ramp element 104. The tooth-attachment element 102 is configured for bonding to the lingual surface of a person's front tooth (e.g., one or more upper or lower incisors and/or canines). In the illustrated embodiment, the ramp element 104 is bendably adjustable relative to the tooth-attachment element 102. The adjustability of the ramp element 104 provides a ramp structure at a desired angle for engaging the corresponding tooth of the opposite dental arch upon closing the person's mouth.

The adjustable bite ramps 100 may be made from metal, plastic, or another suitable material (e.g., a strip crown) so as to allow adjustment of the ramp structure. Suitable metals include stainless steel, titanium, and titanium alloys. Preferably, any metals used are substantially nickel free or have a low nickel content so as to avoid patient sensitivity which can sometimes be caused by nickel. According to one embodiment, the adjustable ramps may be injection molded from a plastic.

Figure 1B:
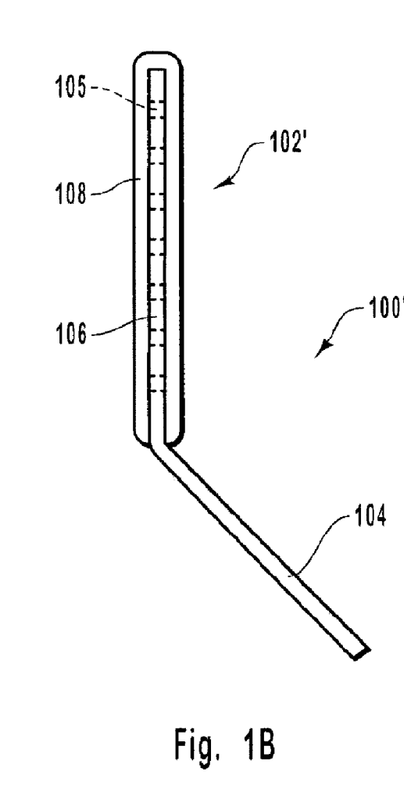
FIG. 1B is a perspective view of an alternative adjustable bite ramp according to the invention.

FIG. 1B illustrates an alternative embodiment of an adjustable bite ramp 100'. Adjustable bite ramp 100' includes a tooth-attachment element 102' and a ramp element 104. The tooth-attachment element 102 comprises an underlying support structure 106 that is integrally attached to the ramp element 104 and that further includes a polymer cover 108 that is overmolded over at least a portion of the support structure 106. The support structure 106 may include holes or perforations 105 [(not shown)] that aid in mechanically interconnecting the overmolded polymer cover 108 over the support structure 106. One purpose of the polymer cover 108 is to provide a bonding surface that is more chemically compatible with adhesive bonding agents that may be used to adhere the tooth-attachment element 102' to a person's tooth during use. In addition, it provides a more comfortable surface for the soft tissues and the tongue when installed. The polymer cover 108' may optionally include undercuts (not shown) in order to promote better interaction and bonding between the polymer cover 108 and an adhesive. According to one embodiment, the polymer cover 108+ may be curved to match the curvature of the lingual surface of an upper incisor (or other tooth).

III. Exemplary Method of Use

Figure 2A:
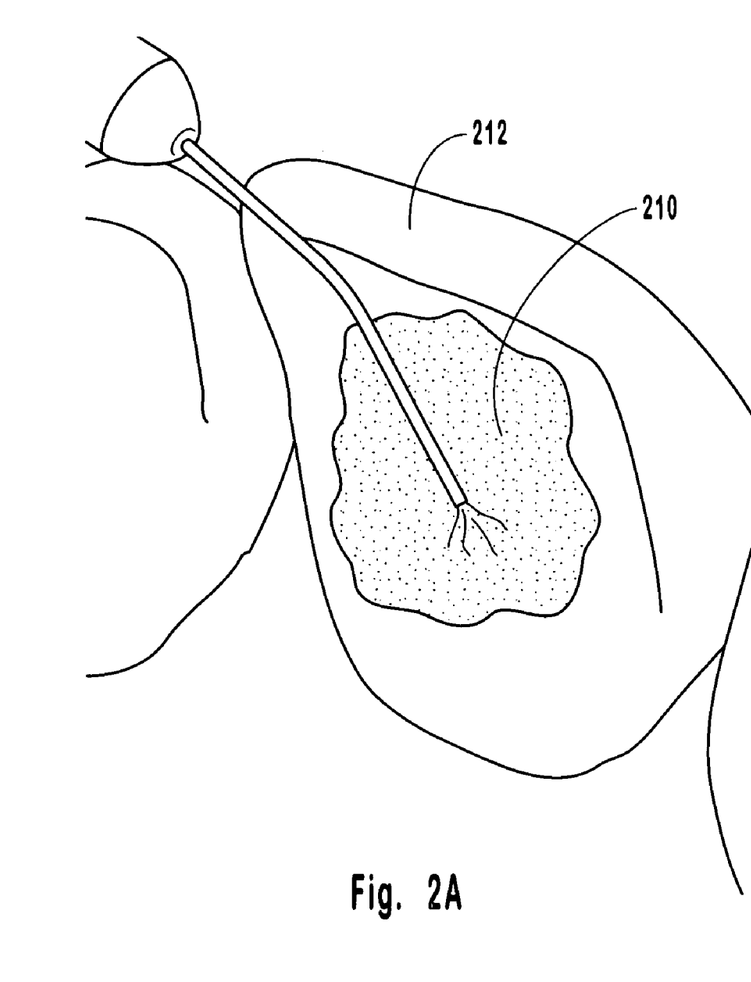
FIGS. 2A-2E depict installation of an adjustable bite ramp.
Figure 2B:
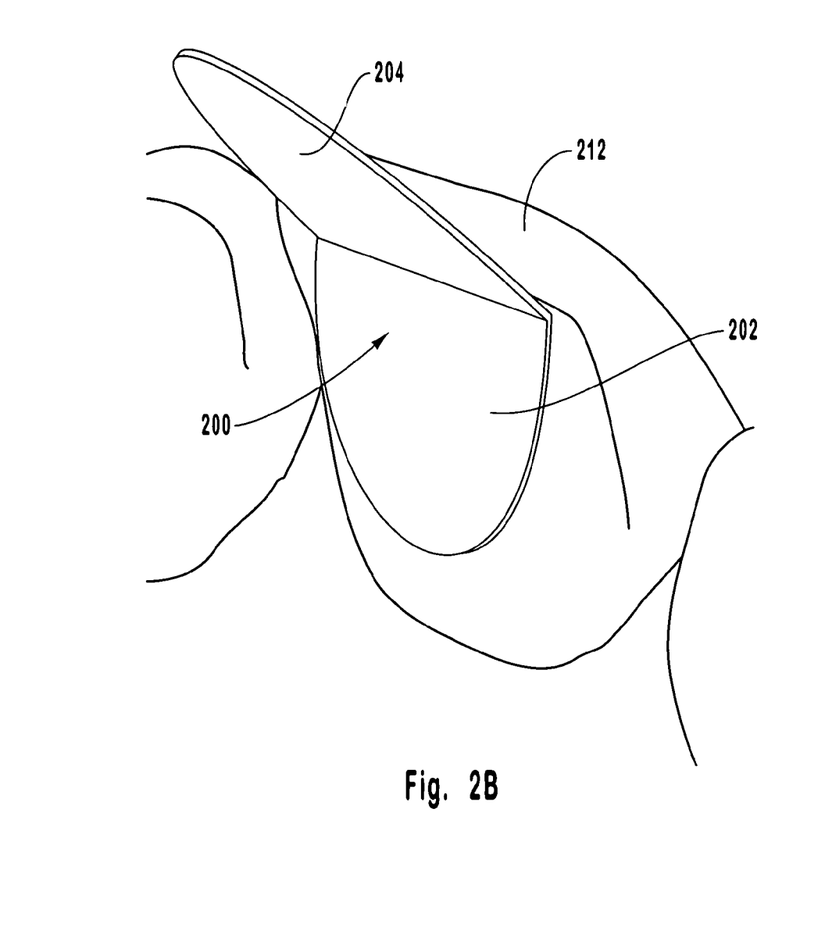

FIGS. 2A-2E illustrate an exemplary method of attaching the adjustable bite ramp 200 to a tooth. FIG. 2A shows an adhesive 210 being applied to the lingual surface of an upper incisor 212. The tooth-attachment element 202 of an adjustable bite ramp 200 is then positioned as desired on the lingual surface of incisor 212, as illustrated in FIG. 2B. Adhesive 210 may be any light or chemically curable adhesive resin known in the art of dentistry to adhere an appliance to a tooth.

Figure 2C:
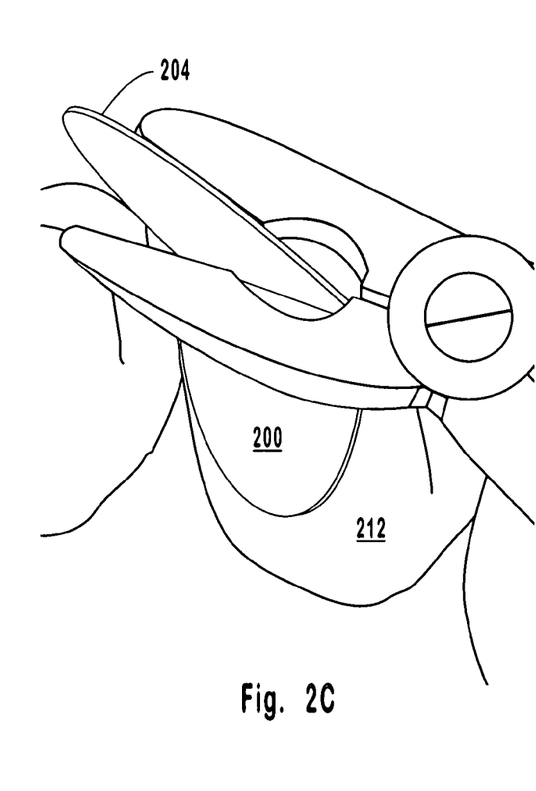

The ramp element 204 of adjustable bite ramp 200 is then adjusted (e.g., by bending) to provide a ramp structure at a desired angle, as illustrated in FIG. 2C. Any suitable tool for adjusting the ramp angle may be used (e.g., pliers, probes, or even a finger).

Figure 2D:
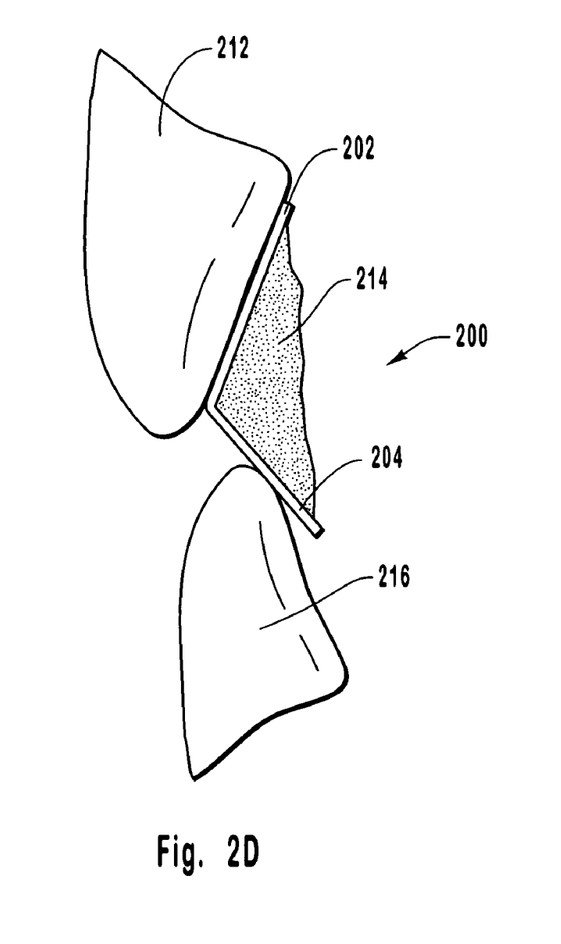
Figure 2E:
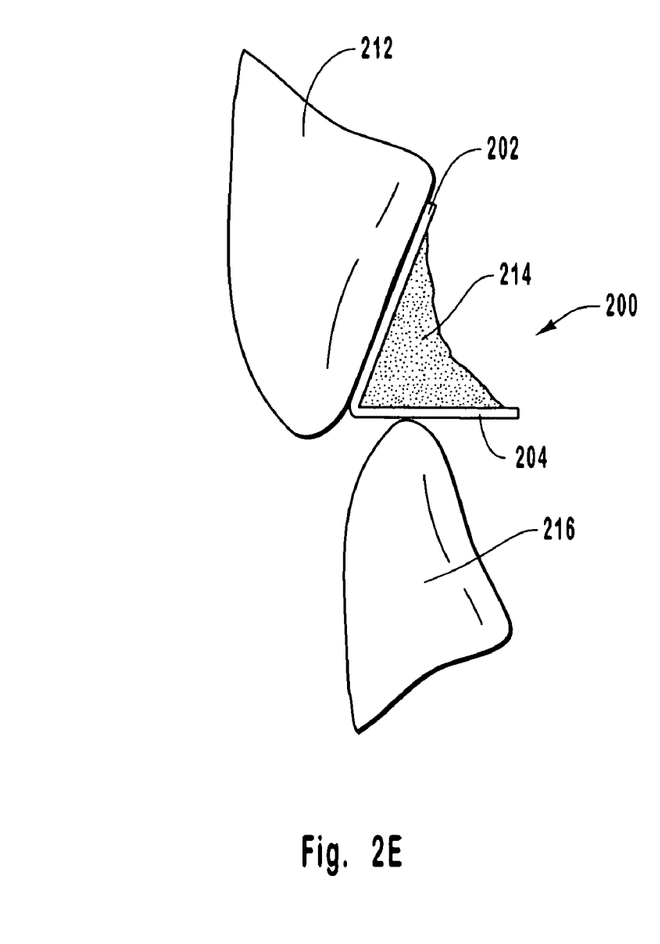

Once the ramp element 204 has been adjusted as desired, the area between the tooth-attachment element 202 and ramp element 204 of adjustable bite ramp 200 may be filled with a light or chemically curable composition 214 (e.g., a filled composite resin used to fill teeth or a luting cement). The composition 214 is cured and hardened so as to lock the ramp element 204 in the desired adjustment angle relative to tooth-attachment element 202, as illustrated in FIG. 2D-2E. Such a curable composition 214 is an example of means for locking a ramp element in a desired adjustment angle relative to a tooth-attachment element.

FIG. 2D also illustrates how the adjustable bite ramp 200, more particularly the ramp element 204, engages the lower incisor 216 as the person's mouth is closed. The engagement between the ramp element 204 and the lower incisor 216 applies a force causing a person's lower jaw to move forward relative to the upper jaw.

The ramp element 204 of adjustable bite ramp 200 may be adjusted to provide a ramp structure at any desired angle. FIG. 2D illustrates the ramp element 204 having been adjusted so as to provide an oblique angle between the tooth-attachment element 202 and the ramp element 204. FIG. 2E alternatively illustrates a ramp element 204 having been adjusted so as to provide an acute angle between the tooth-attachment element 202 and the ramp element 204. The exact angle between the ramp element 204 and tooth-attachment element 202 may be selected depending on one or more of the relative positions of the upper and lower jaws, size of the person's teeth, angle of the teeth, desired degree of correction, and the like.

Figure 3A:
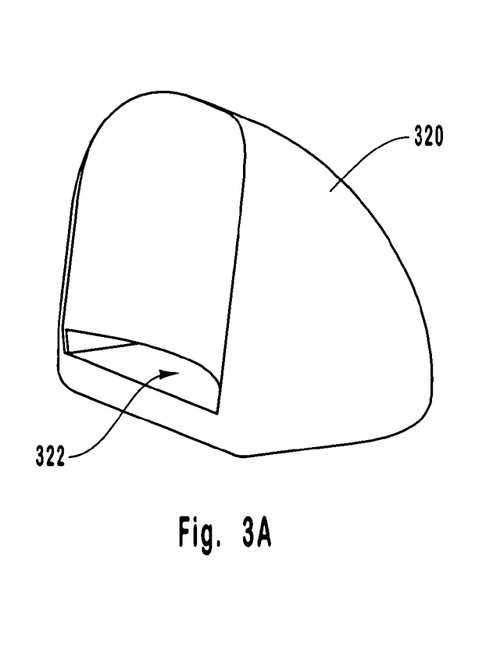
FIGS. 3A and 3B depict an optional shoe that may be used in association with an adjustable bite ramp.
Figure 3B:
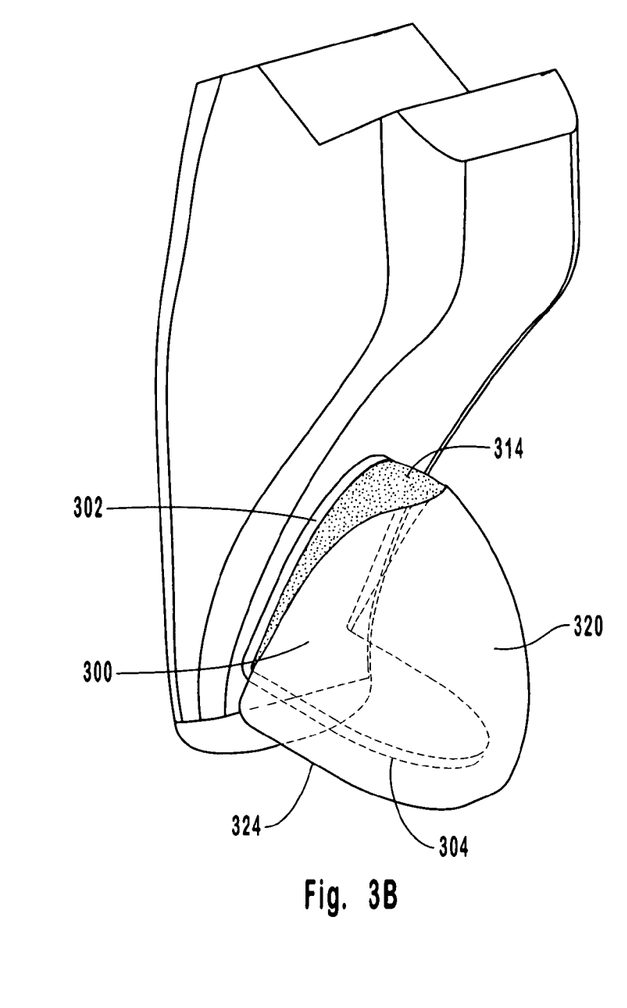

The adjustable bite ramps of the invention may optionally be used in combination with a shoe. FIGS. 3A and 3B illustrate an optional shoe 320 for use with an adjustable bite ramp 300. The shoe 320 may be placed over the ramp element 304 of bite ramp 300, more particularly by inserting ramp element 304 into a receiving slot 322 in the shoe 320. The shoe 320 may be bonded to the adjustable bite ramp 300 by use of an adhesive. When used, a lower surface 324 of the shoe 320 provides a ramp surface for slidable engagement with the corresponding tooth of the opposite dental arch (e.g., the lower incisor). As illustrated, the upper surface of the shoe 320 may be rounded so as to provide a smooth surface for increased patient comfort and/or to prevent build-up of plaque or debris.

The shoe 320 may be adapted to form a flush fit against the person's incisor, more particularly, the tooth-attachment structure 302 of the bite ramp 300. After adjustment of the ramp element 304, a space may exist between the shoe 320 and the tooth-attachment element 302, which is advantageously filled with a curable composition 314.

Figure 4A:
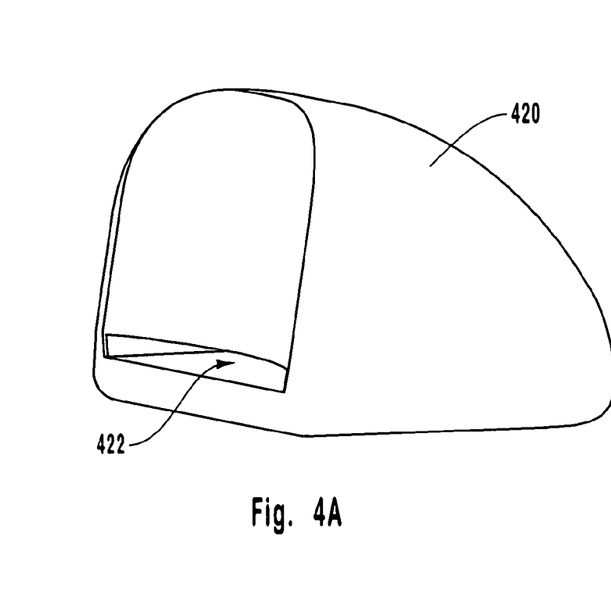
FIGS. 4A and 4B depict an alternative optional shoe that may be used in association with an adjustable bite ramp.
Figure 4B:
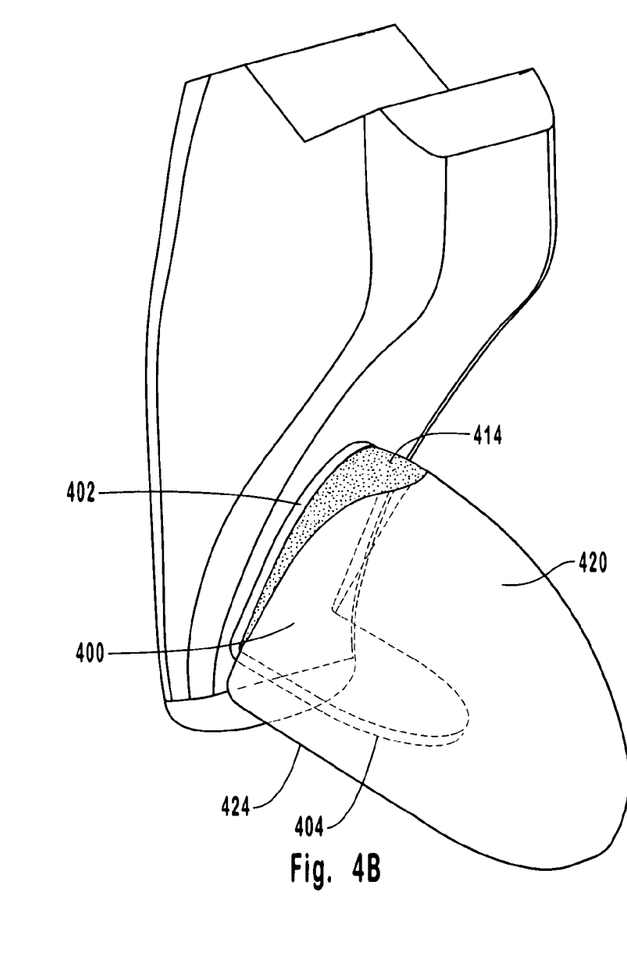

FIGS. 4A and 4B illustrate an alternative embodiment of a shoe 420 that is used in the same manner as shoe 320 illustrated in FIGS. 3A and 3B, except that the lower surface 424 of the shoe 420 is significantly longer than surface 324 of shoe 320. Providing an increased working length of the lower surface 424 may be desirable for treating more severe class II malocclusions.

During treatment, it may be desirable to begin treatment with a longer shoe 420 such as that illustrated in FIGS. 4A-4B. According to one embodiment, the shoe may be formed of a material (e.g., PEEK polyarylether ketone) that will form a weaker bond with the resin 414 used to fill space between the shoe 420 and tooth-attachment element 402 as compared to the bond between the tooth-attachment element 402 or an optional overmolded polymer cover (see FIG. 1B) (e.g., formed of a polymer such as TROGAMID nylon) and the filling resin 414. Using such a material allows preferential separation of the shoe 420 from the filling resin 414. As treatment progresses, the lower jaw is pulled forward. Once the lower jaw has been pulled sufficiently forward, the longer shoe 420 may be removed and replaced with a shorter shoe, such as shoe 320 illustrated in FIG. 3A-3B, which is less intrusive within the mouth of the patient.

Alternatively, treatment may begin with a longer shoe, such as that illustrated in FIGS. 4A-4B, and once the lower jaw has been pulled sufficiently forward, the end of the shoe may be ground or cut so as to form a shoe of a shorter length, which is less intrusive within the mouth of the patient. In addition, the shorter adjustable bite ramp may be used to stabilize an opened bite that has been achieved by earlier treatment. Temporarily continuing use of such a bite ramp prevents the treated teeth from returning to their original untreated configuration.

The bite ramps according to the invention may optionally be used in combination with class II elastics to move the lower jaw forward. According to one method, respective elastics are stretched between the lower end molars and the upper canines.

The present invention may be embodied in other specific forms without departing from its spirit or essential characteristics. For example, it may be desirable to use the adjustable bite ramps in treating medical joint problems. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An adjustable bite ramp for use in an orthodontic treatment, comprising:
    a first portion that is a generally flat, planar surface that is sized and shaped so as to generally conform to the lingual area of a person's front tooth so as to be configured as a tooth-attachment element for bonding entirely behind a person's front tooth to the lingual surface of a person's front tooth;
    a second portion extending as an integral part of the first portion, the second portion being a generally flat, planar surface that essentially mirrors in size and shape the first planar surface but is bendably adjustable relative to the first planar surface along a common bend line, the second planar surface of the adjustable bite ramp being configured so that once it is bent relative to the first planar surface configured as a tooth-attachment element, the second planar surface will be configured as a ramp element that is bent at a desired angle for engagement with a corresponding tooth of the opposite dental arch upon closing a person's mouth during use; and
    means for locking said ramp element in a desired adjustment angle relative to said tooth-attachment element.

2. An adjustable bite ramp as recited in claim 1, said tooth-attachment element having holes or perforations formed therein.

3. An adjustable bite ramp as recited in claim 2, further comprising a polymer cover that is overmolded over at least a portion of said tooth-attachment element, said holes or perforations assisting in retaining the polymer cover over said tooth-attachment element.

4. An adjustable bite ramp as recited in claim 1, wherein said means for locking said ramp element comprises a curable composition applied to and cured between said tooth-attachment element and said ramp element.

5. An adjustable bite ramp as recited in claim 1, wherein said tooth-attachment element and said ramp element are formed from one of stainless steel, titanium, or a titanium alloy.

6. An adjustable bite ramp as recited in claim 1, wherein said tooth-attachment element and said ramp element are formed by injection molding a plastic.

7. An adjustable bite ramp as recited in claim 1, further comprising an overmolded polymer cover comprising a polyamide over at least a portion of said tooth-attachment element.

8. An adjustable bite ramp as recited in claim 7, wherein said polymer cover has a curvature corresponding to a curvature of the lingual surface of a person's upper incisor.

9. An adjustable bite ramp as recited in claim 1, further comprising a shoe removably connected to said ramp element.

10. An adjustable bite ramp as recited in claim 9, said shoe having a flat lower surface for engagement with a person's corresponding tooth of the opposite dental arch, and a rounded upper surface.

11. An adjustable bite ramp as recited in claim 9, said shoe including a slot for receiving said ramp element during attachment of said shoe over said ramp element.

12. An adjustable bite ramp as recited in claim 1, said ramp element having an angle such that the bite ramp is able to cause a person's lower jaw to move forward relative to the person's upper jaw upon closing the person's mouth during use.

13. An adjustable bite ramp kit for use in an orthodontic treatment, comprising
    a plurality of adjustable bite ramps, each comprising
        a first portion that is a generally flat, planar surface that is sized and shaped so as to generally conform to the lingual area of a person's front tooth so as to be configured as a tooth-attachment element for bonding entirely behind a person's front tooth to the lingual surface of a person's front tooth; and
        a second portion extending as an integral part of the first portion, the second portion being a generally flat, planar surface that essentially mirrors in size and shape the first planar surface but is bendably adjustable relative to the first planar surface along a common bend line, the second planar surface of the adjustable bite ramp element being configured so that once it is bent relative to the first planar surface configured as a tooth-attachment element, the second planar surface will be configured as a ramp that is bent at a desired angle for engagement with a corresponding tooth of the opposite dental arch upon closing a person's mouth during use; and
    wherein the kit further comprises a curable resin comprising an adhesive resin for adhesively attaching at least one said bite ramp to a patient's teeth during use.

14. A kit as recited in claim 13, wherein said curable resin comprises a curable composite composition for use in locking said ramp element in a desired adjustment angle relative to said tooth-attachment element.

15. A kit as recited in claim 13, further comprising a shoe comprising a polyaryletherketone shoe configured for placement over said adjustable bite ramp.

16. A kit as recited in claim 15, wherein said shoe has a flat lower surface for engagement with a person's corresponding tooth of the opposite dental arch, and a rounded upper surface.

17. A kit as recited in claim 15, said shoe including a slot for receiving said ramp element during attachment of said shoe over said bite ramp.

18. A kit as recited in claim 15, the kit comprising a plurality of differently-sized shoes, each shoe being configured for placement over said adjustable bite ramp.

19. A kit as recited in claim 13, further comprising at least one class II elastic.

20. An adjustable bite ramp kit as defined in claim 13, wherein the kit also includes at least one shoe configured for placement over at least one said adjustable bite ramp.

21. A kit as recited in claim 20, said shoe having a flat lower surface for engagement with a person's corresponding tooth of an opposite dental arch, and a rounded upper surface.

22. A kit as recited in claim 20, the kit comprising a plurality of differently-sized shoes, each shoe being configured for placement over a set of adjustable bite ramp.

23. A kit as recited in claim 20, further comprising at least one class II elastic.

* * * * *